United States Patent [19]

Sussman

[11] Patent Number: 5,069,663
[45] Date of Patent: Dec. 3, 1991

[54] HYDROCEPHALUS VALVE

[75] Inventor: Marvin L. Sussman, Miami, Fla.

[73] Assignee: Cordis Corporation, Miami Lakes, Fla.

[21] Appl. No.: 681,414

[22] Filed: Apr. 4, 1991

Related U.S. Application Data

[63] Continuation of Ser. No. 443,058, Nov. 28, 1989, abandoned, which is a continuation of Ser. No. 255,790, Oct. 11, 1988, abandoned.

[51] Int. Cl.$^5$ .............................................. A61M 27/00
[52] U.S. Cl. ........................................ 604/9; 604/247
[58] Field of Search ................................ 604/840, 247

[56] References Cited

U.S. PATENT DOCUMENTS

| | | | |
|---|---|---|---|
| 3,288,142 | 11/1966 | Hakim | 604/9 |
| 3,527,226 | 9/1970 | Hakim | 604/9 |
| 3,889,687 | 6/1975 | Harris et al. | 604/10 |
| 3,985,140 | 10/1976 | Harris | 604/9 |
| 4,332,255 | 6/1982 | Hakim et al. | 604/9 |
| 4,413,985 | 11/1983 | Wellner et al. | 604/9 |
| 4,595,390 | 6/1986 | Hakim et al. | 604/9 |
| 4,850,955 | 7/1989 | Newkirk | 604/9 |
| 4,867,741 | 9/1989 | Portnoy | 604/10 |
| 4,883,456 | 11/1989 | Holter | 604/9 |

OTHER PUBLICATIONS

Medos–"The Medos TM Nonprogrammable Hakim Valve System"–Sep. 1987–Information Manual.
"Cordis Integral Shunt System" Copyright Jun. 1987.
"Nonprogrammable Hakim Valve System for the Control of Hydrocephalus".

Primary Examiner—John D. Yasko
Assistant Examiner—Adam J. Cermak
Attorney, Agent, or Firm—Watts, Hoffmann, Fisher & Heinke CO.

[57] ABSTRACT

A hydrocephalus valve for relieving pressures in the brain by draining cerebrospinal fluid. The valve is coupled at an inlet end to a ventricular catheter for routing fluid from the brain and delivering that fluid to another body region. An outlet portion of the valve unit is coupled to a drainage catheter. Two different construction valves form a valve mechanism that regulates fluid flow from the brain. An inlet valve comprises a check valve to facilitate pumping of the valve unit and in addition, helps break up proteins suspended within the cerebrospinal spinal. At an outlet portion, a pressure control valve having a coiled spring for biasing a ball against a valve seat, controls pressure of the cerebrospinal fluid as it exits the valve mechanism and is delivered to the drainage catheter.

6 Claims, 1 Drawing Sheet

HYDROCEPHALUS VALVE

This is a continuation of copending applications Ser. No. 07/443,058 filed on Nov. 28, 1989, (abandoned), which is a continuation of Ser. No. 07/255,790 filed on Oct. 11, 1988 (abandoned).

TECHNICAL FIELD

The present invention relates to a cerebrospinal fluid drainage system for relieving fluid pressures that reach excessive levels in the brain.

BACKGROUND ART

U.S. Pat. Nos. 3,288,142 and 3,527,226 to Hakim relate to catheter systems for relieving pressure build up within the brain. These patents disclose systems that continuously control drainage of cerebrospinal fluid from the brain and release that fluid into the body. As seen most clearly in FIGS. 1 and 3 of the '226 patent to Hakim, one process for draining fluid away from the brain utilizes a valve unit having entrance and exit valves respectively. This allows the valve unit to be used as a pump to help unclog a blocked drainage catheter.

Both valves within the valve unit of the '226 patent are the same. They utilize a corrugated or convoluted spring element for biasing a trapped ball against a fluid inlet seat of the valve. Experience with the valve units shown in the '226 patent indicate the pressure at which fluid exits the brain using such a valve may be difficult to control.

Each pressure relief system must be evaluated prior to implantation within the subject since different pressures are chosen for different subjects depending upon the needs of that individual. If the valve pressure varies from its rated value, fluid pressures may rise or fall to dangerous levels.

Valve systems for ventricular shunting are discussed in a prior art publication entitled "Cordis Integral Shunt System", Copyright June, 1987. This publication is incorporated herein by reference. In this publication, the valve unit discussed in the '226 prior art patent noted above is characterized as a standard Hakim mechanism. A second unit characterized as a pediatric Hakim mechanism is also disclosed in the Cordis publication. This unit also includes two valves mounted within a valve housing for controlling pressure of fluid routed away from the brain to a drainage site. The two valves in the pediatric unit result in more uniform regulation of the fluid pressure passing through the unit.

Both valves in the pediatric Hakim mechanism include a coiled spring trapped between a valve body and a ball which selectively opens and closes against a valve body seat. The pediatric valve mechanisms are adjustable and experience with the pediatric unit suggests more accurate fluid pressure control is possible. A disadvantage, however, has been noticed with functioning of the pediatric unit depicted in the Cordis publication. High concentrations of protein may be suspended within the fluid routed away from the brain. This protein can clog the passageways in the valve unit resulting in an unstable operation. If the clogged portion is at the exit side of the valve unit, pumping action may successfully unblock the valve. If, however, the clogging occurs on the inlet valve, the blockage is not so easily opened.

DISCLOSURE OF THE INVENTION

The present invention relates to a system for relieving pressure build up within a subject's brain by use of a catheter system utilizing a valve unit having a hybrid configuration. In accordance with the invention, the valve unit has a housing defining an enclosure in which are mounted two valves, one an inlet valve and a second outlet valve. The inlet valve is similar in construction to the Hakim valve shown in the '226 patent. A corrugated spring biases a ball within an inlet seat. This first valve acts as a check valve to allow pumping of fluid inside the unit by the application of pressure to the housing. The ball is forced against the check valve seat but prevented from movement within the housing by the corrugated spring unit.

A valve unit outlet includes a valve having a valve body and a screw insert which traps a spring between the valve body and a ball seated against the valve body inlet. This is similar to the valves shown in the Cordis Pediatric Hakim mechanism. The compression of the spring is adjusted during manufacture of the unit by rotating the screw insert with respect to the valve body. This construction enables the pressure of fluid passing through the valve unit to be controlled quite closely without clogging of the unit. The relatively low pressure control on the inlet portion of the valve unit tends to break up suspended proteins to avoid clogging of the outlet valve. These and other objects, advantages and features of the invention will become better understood from a detailed description of the invention which is described in conjunction with a preferred embodiment.

BEST MODE FOR CARRYING OUT THE INVENTION

Figure 1:
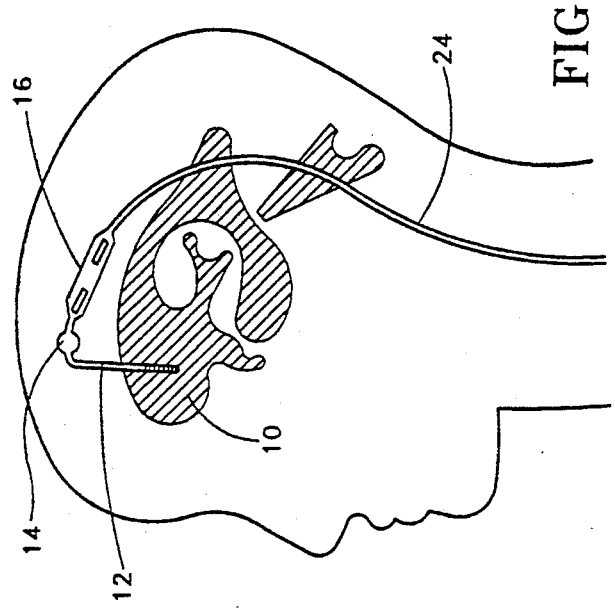
FIG. 1 is a schematic representation showing a drainage system for relieving pressures within a subject's brain.
Figure 2:
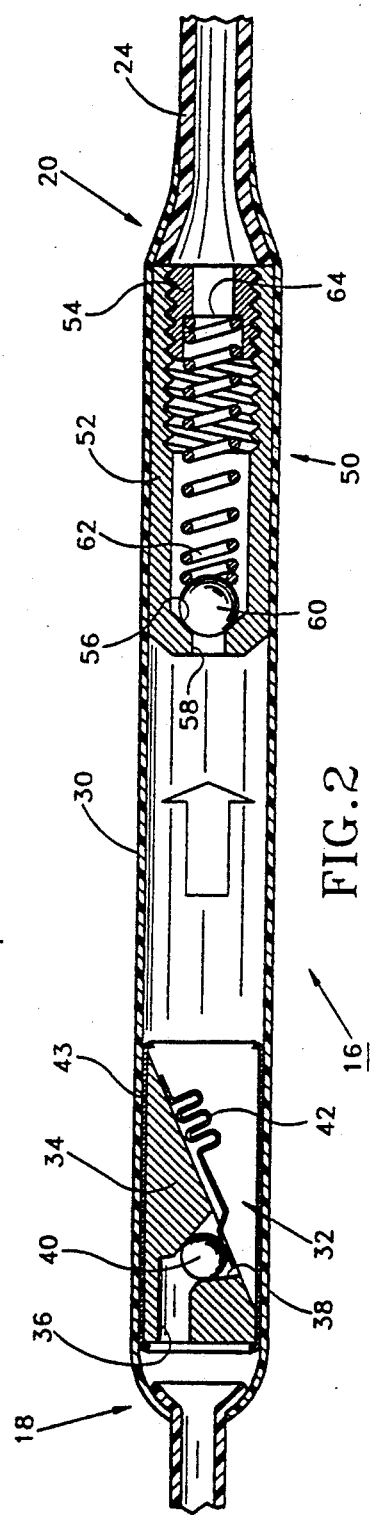
FIG. 2 is a section view of a valve unit coupled to a catheter for routing fluid away from the brain and in addition having an outlet coupled to a catheter which drains the fluid from the brain into a drainage site in the subject.

Turning now to the drawings, FIG. 1 shows a catheter system for routing fluid away from a subject's brain 10 through a ventricular catheter 12 implanted using procedures described in the aforementioned brochure entitled "Cordis Integral Shunt System". The ventricular catheter defines an ante-chamber 14. Fluid exiting the antechamber 14 or a burr hole reservoir enters a valve unit 16 depicted in more detail in FIG. 2.

The valve unit 16 includes an inlet 18 downstream from the antechamber 14. An outlet 20 leads to a drainage catheter 24 which discharges cerebrospinal fluid into the subject's body. Details regarding the surgical placement of this unit are found in the "Cordis Integral Shunt System" brochure.

In the system disclosed in FIG. 1, both catheters are integrally connected to the valve unit 16. The ventricular catheter 12 is a radiopaque, silicone elastomer ventricular catheter which has been treated with a barium sulphate material to enhance visualization of the catheter during implant. The drainage catheter 24 also comprises a silicone elastomer catheter substantially longer than the ventricular catheter to deliver fluid draining from the brain through the valve unit to a suitable drainage site such as the subject's peritoneal cavity or the right atrium of the heart.

The valve unit 16 is housed within a silicone elastomer housing 30 having a cylindrical outer wall that is attached to the ventricular and drainage catheters through techniques known in the art. One technique is to attach the housing 30 to the catheters with a glue that bonds the catheter and housing 30.

The housing 30 defines an interior chamber having an inlet end and an exit end in fluid communication with the ventricular and drainage catheters, respectively. A check valve 32 is located at the inlet end of the chamber and includes a stainless steel body 34 defining an inlet channel 36 leading to a cone-shaped valve seat 38. The body 34 is supported within a stainless steel cylinder 43 that engages the housing interior and orients the valve body 34. Fluid exiting the antechamber 14 enters the valve inlet 36 and passes through the cone-shaped seat 38 under control of a ball 40 held within the seat by a convoluted spring 42. The spring is attached to the valve body 34 by a suitable connection (not shown) at an end of the spring 42 removed from the valve seat 38. At an opposite end the spring 42 defines a flat segment that engages the ball 40 and holds it in place.

The valve 32 acts as a check valve and does not significantly limit fluid passage into the housing of the valve unit 16. It does, however, break up protein solids carried by the cerebrospinal fluid entering the valve unit 16.

Downstream from the inlet or check valve 32 a pressure control valve 50 dictates fluid pressure of the cerebrospinal fluid leaving the unit 16. The valve 50 has a stainless steel tubelike valve body member 52, and a stainless steel screw insert 54 which threadingly engage in a way to define the pressure of the fluid exiting the valve. The insert 54 has a stepped inner diameter which defines a circular ridge. The outer valve body tube 52 extends axially along the valve unit 16 and defines a cone-shaped valve seat 56 and inlet 58. A ball 60 is biased towards the valve seat 56 by a coiled spring 62 trapped between a ridge 64 of the insert 54 and the valve seat 56 defined by the outer member 52. By adjusting the length between the ball 60 and the ridge 64 that engages the spring 62, the force applied to the ball 60 by the coiled spring 62 can be adjusted. Prior to insertion of the valve 50 into the housing 30 the valve body members 52 and insert 54 are relatively rotated to adjust the compression force of the spring to a desired value. Fluid entering the check valve 32 passes through the housing chamber of the valve unit 16 to the valve inlet 58 of the second valve 50. When pressure builds to a value sufficient to overcome the forces exerted by the spring 62 and ball 60 on the valve seat 56, the fluid exits the valve unit 16 by the drainage catheter 24. The two valve balls 40, 60 are constructed of ruby which is synthetically manufactured. The springs 42, 62 are stainless steel as are the valve bodies 34, 52, 54.

The inlet valve acts as essentially a check valve so that fluid exiting the brain and the antechamber 14 (FIG. 1) enters the housing 30 (FIG. 2) via the inlet valve 32 and exits the valve unit 16 in a controlled way through adjustment of the outlet valve 50. Passage of the fluid through the inlet valve 32, however, tends to break up the proteins carried in suspension by the fluid and results in more reliable, trouble free flow of the fluid through the second valve 50.

In the event the valve unit 16 becomes clogged due to protein build up within the outlet valve 50, as is well known in the art it is possible for the unit to be pumped by applying a pressure to the flexible housing 30. Such pressure closes the check valve 32 while forcing entrapped fluids and proteins through the exit valve 50 at a high pressure sufficient to unclog that valve.

The present invention has been described with a degree of particularity. It is the intent, however, that the invention include all modifications and alterations from the disclosed design falling within the spirit or scope of the appended claims.

I claim:

1. Valve apparatus for use in routing cerebrospinal fluid away from the brain at a controlled pressure; said valve apparatus comprising an implant defining a chamber having an inlet and an outlet, said inlet for routing cerebrospinal fluid from the brain into the chamber and said outlet for routing said cerebrospinal fluid from the chamber to a drainage location within a subject; said implant comprising
   i) an inlet value located at an inlet end of the chamber to allow cerebrospinal fluid to enter the chamber and to impede reverse flow of the cerebrospinal fluid from the chamber, said inlet valve comprising an inlet valve body that defines a seat, a ball that moves toward and away from said seat in response to fluid passing through said inlet valve and a corrugated cantilever spring attached at one end to the inlet valve body and having a ball engaging surface at an opposite end of said spring tending to hold the ball against said seat; and
   ii) an outlet valve located downstream from the inlet valve and comprising an outlet valve body defining a outlet valve seat, a ball dimensioned to close off the outlet valve seat, and a coiled spring trapped between the ball and the control valve body to bias the ball against the outlet valve seat and means for adjusting the length of the coiled spring between the ball and a shoulder that engages the coiled spring to regulate the pressure of the fluid passing from the chamber through the chamber outlet.

2. The apparatus of claim 1 additionally comprising a ventricular catheter having one end implanted in the brain and an opposite end coupled to the inlet and a drainage catheter having one end coupled to the outlet and having an opposed end positioned at a fluid drainage site.

3. The valve apparatus of claim 1 wherein the outlet valve body comprises:
   a) an outer valve body portion that defines a fluid passageway and includes a threaded interior wall along at least a portion of the fluid passageway; said outer valve body portion defining the outlet valve seat; and
   b) a threaded insert for threadingly engaging the threaded interior wall of the outer valve body portion and defining a shoulder which engages the coiled spring to trap the coiled spring between the shoulder and the ball and thereby bias the ball against and the outlet valve seat.

4. A method for draining cerebrospinal fluid from the brain comprising the steps of:
   a) routing the cerebrospinal fluid from the brain through a catheter to a chamber through a check valve having a ball biased into a valve seat by an elongated corrugated cantilever spring fixed at one end and contacting the ball at an opposite end; said check valve allowing cerebrospinal fluid to enter the chamber in a flow pattern tending to break up clogs in the cerebrospinal fluid entering the chamber through the check valve; and b) regulating flow of cerebrospinal fluid from the chamber to a drainage catheter for delivering the cerebrospinal fluid to a drainage site by forming a restriction at an exit from the chamber and biasing a ball against the restriction with a compression spring; said regulating step performed by adjusting the compression of the compression spring such that cerebrospinal fluid exits the chamber at a controlled pressure.

5. The method of claim 4 wherein the biasing of the ball is performed by trapping a compressed spring between the ball and an end wall of said chamber.

6. Valve apparatus for use in routing cerebrospinal fluid away from the brain at a controlled pressure; said valve apparatus comprising:

a) an implant defining a chamber having an inlet and an outlet, said inlet for routing cerebrospinal fluid from the brain into the chamber and said outlet for routing said cerebrospinal fluid from the chamber to a drainage location within a subject;

b) an inlet valve supported by the implant at an inlet end of the chamber to allow cerebrospinal fluid to enter the chamber and to impede reverse flow of the cerebrospinal fluid from the chamber back to the brain, said inlet valve comprising an inlet valve body that defines a seat, a ball that moves toward and away from said seat in response to fluid passing through said inlet valve and corrugated cantilever spring attached at one end to the inlet valve body and having a ball engaging surface at an opposite end of the cantilever spring tending to hold the ball against said seat; and c) an outlet valve supported by the implant within the chamber downstream from the inlet valve and comprising an outlet valve body having an outlet valve body portion member that defines an outlet valve seat and a threaded interior wall defining a flow path downstream from the outlet valve seat, a ball for regulating fluid flow through the outlet valve seat, a threaded insert that threadingly engages the threaded interior wall of the outlet valve body and having a shoulder that defines a portion of the fluid flow path and a coiled spring trapped between the ball and the shoulder of the threaded insert to bias the ball against the control valve seat and wherein the length of the coiled spring is adjusted to control the pressure at which the fluid exists the outlet valve.

* * * * *